(12) United States Patent
Barnes

(10) Patent No.: US 6,967,008 B1
(45) Date of Patent: Nov. 22, 2005

(54) OZONE GENERATOR AND LIGHT SOURCE FOR ENCLOSED SPACES

(76) Inventor: Ronald L. Barnes, #74 Revere Way, Huntsville, AL (US) 35801-2846

( * ) Notice: Subject to any disclaimer, the term of this patent is extended or adjusted under 35 U.S.C. 154(b) by 353 days.

(21) Appl. No.: 10/176,299

(22) Filed: Jun. 20, 2002

Related U.S. Application Data

(63) Continuation-in-part of application No. 10/061,752, filed on Feb. 1, 2002, now Pat. No. 6,723,233, which is a continuation-in-part of application No. 09/752,982, filed on Dec. 31, 2000, now Pat. No. 6,623,635, which is a continuation-in-part of application No. 09/418,915, filed on Oct. 15, 1999, now Pat. No. 6,342,154, said application No. 10/061,752 is a continuation-in-part of application No. 09/794,601, filed on Feb. 27, 2001, now abandoned, which is a continuation-in-part of application No. 09/752,982, and a continuation-in-part of application No. 09/717,904, filed on Nov. 20, 2000, now Pat. No. 6,426,053, and a continuation-in-part of application No. 09/520,504, filed on Mar. 8, 2000, now Pat. No. 6,405,387, and a continuation-in-part of application No. 09/393,437, filed on Sep. 10, 1999, now Pat. No. 6,192,911, application No. 10/176,299, which is a continuation-in-part of application No. 09/794,601, and a continuation-in-part of application No. 09/717,903, filed on Nov. 20, 2000, now Pat. No. 6,428,756.

(60) Provisional application No. 60/166,254, filed on Nov. 18, 1999.

(51) Int. Cl.⁷ .............................................. B01J 19/08

(52) U.S. Cl. .......................... 422/186.12; 422/186.07; 422/121

(58) Field of Search ...................... 422/186.07, 186.12, 422/121

(56) References Cited

U.S. PATENT DOCUMENTS

| 4,309,388 | A | * | 1/1982 | Tenney et al. | ............... | 422/304 |
| 6,458,257 | B1 | * | 10/2002 | Andrews et al. | ............ | 204/263 |

FOREIGN PATENT DOCUMENTS

| JP | 56-045806 A | * | 4/1981 |
| JP | 05-071861 A | * | 3/1993 |
| JP | 09-172959 A | * | 7/1997 |
| JP | 11-206316 A | * | 8/1999 |

\* cited by examiner

Primary Examiner—Kishor Mayekar
(74) Attorney, Agent, or Firm—Mark Clodfelter

(57) ABSTRACT

An ozone generator that serves the double functions of providing a light source and providing ozone is disclosed. Particularly, the ozone generator may be located in a generally closed appliance, such as a refrigerator, dishwasher, clothes washer or drier or the like. In addition, a stand-alone embodiment is disclosed that may simply be mounted or placed in storage or other areas such as closets, pantries, laundry rooms, clothes hampers, bed linen storage trunks and others. In some embodiments, timers are used to periodically raise ozone levels to relatively high levels and then allow the levels to fall, sanitizing and deodorizing the areas within which they are located. In other embodiments, advanced oxidation techniques are used by using a pair of ultraviolet tubes, one emitting radiation at a wavelength of 185 nm and the other emitting radiation at 254 nm.

22 Claims, 7 Drawing Sheets

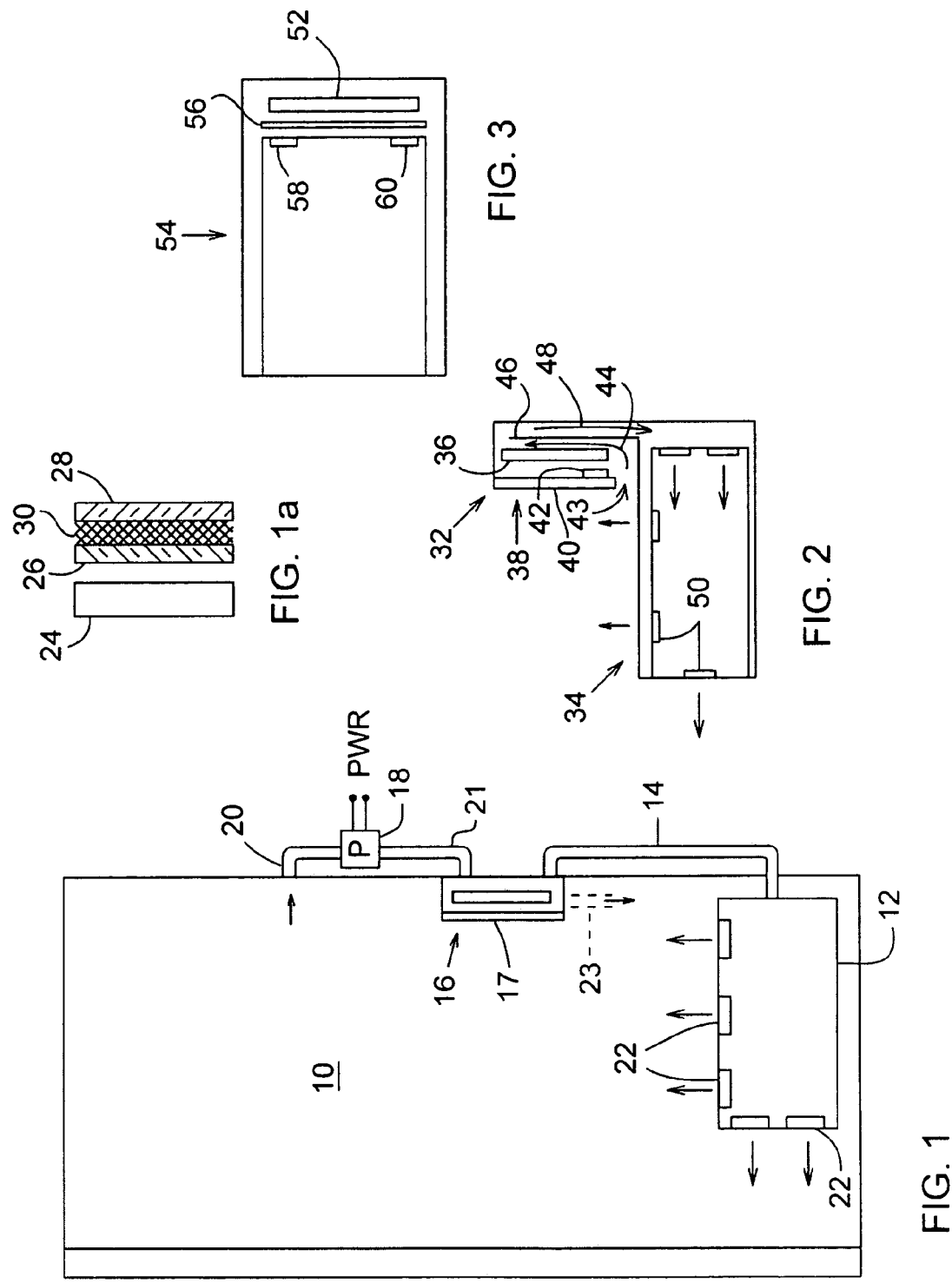

OZONE GENERATOR AND LIGHT SOURCE FOR ENCLOSED SPACES

CROSS REFERENCE TO RELATED APPLICATIONS

This application is a continuation-in-part application of application Ser. No. 09/717,903, filed Nov. 20, 2000 now U.S. Pat. No. 6,428,756, which claims the benefit of provisional application No. 60/166,254, filed Nov. 18, 1999. This application also is a continuation-in-part of patent application Ser. No. 09/794,601, filed Feb. 27, 2001 now abandoned, which is a continuation-in-part of patent application Ser. No. 09/752,982, filed Dec. 31, 2000 now U.S. Pat. No. 6,623,635, and a continuation-in-part of patent application Ser. No. 09/393,437, filed Sep. 10, 1999, now U.S. Pat. No. 6,192,911. This application is also a continuation-in-part of patent application Ser. No. 10/061,752, filed Feb. 1, 2002 now U.S. Pat. No. 6,723,233, which is a continuation-in-part, of patent application Ser. No. 09/752,982, filed Dec. 31, 2000 now U.S. Pat. No. 6,623,635, which is a continuation-in-part of patent application Ser. No. 09/418,915, filed Oct. 15, 1999, now U.S. Pat. No. 6,342,154, and which is a continuation-in-part of patent application Ser. No. 09/794, 601, filed Feb. 27, 2001 now abandoned, which is a continuation-in-part of patent application Ser. No. 09/752,982, filed Dec. 31, 2000 now U.S. Pat. No. 6,623,635, and a continuation-in-part of patent application Ser. No. 09/393, 437, filed Sep. 10, 1999, now U.S. Pat. No. 6,192,911, and a continuation-in-part of patent application Ser. No. 09/520, 504, filed Mar. 8, 2000 now U.S. Pat. No. 6,405,387, and a continuation-in-part of patent application Ser. No. 09/717, 904, filed Nov. 20, 2000 now U.S. Pat. No. 6,426,053.

FIELD OF THE INVENTION

This application relates to providing ozone and illumination to enclosed areas in need of sterilization or deodorization such as interiors of certain large appliances, closets or the like.

BACKGROUND OF THE INVENTION

It is well known that certain large appliances, such as refrigerators and dishwashers, in addition to other enclosed spaces such as pantries, closets, dirty clothes hampers, clothes and bed linen storage receptacles and similar such receptacles and appliances may in certain instances develop a dank, moldy odor or, in the instances of pantries or clothes or bed linen receptacles, contain a certain amount of insect pests such as cockroaches, flour weevils, moths, etc. In some of these closed areas the odor or insects are simply a nuisance, and in others a genuine health hazard or likelihood of damage to goods is present. Particularly, in the instance of a refrigerator, fruit contained in a "crisper" portion of the refrigerator may produce certain gasses, such as methane, or for tomatoes acetylene, that ripen the fruit prematurely. Vegetables in a crisper may also develop mold, which may produce ruination of everything in the crisper. In addition, food left beyond its time in a refrigerator may spoil or sour, producing foul odors that may permeate into other food, or if the refrigerator is provided with an automatic icemaker, into the water for ice, rendering the food and/or ice unpalatable.

In other appliances, such as dishwashers, dishes may be inadvertently left in a dishwasher too long, resulting in unwashed food on the dishes and utensils becoming spoiled, which also produces foul odors and gasses such as methane. While not particularly dangerous inasmuch as most modern dishwashers heat water to a sanitizing level sufficient to kill microorganisms, the outpouring of noxious odors when a door of such a dishwasher is opened is unpleasant, and may be nauseating. A similar occurrence may occur in the instance of clothes washers, and clothes dryers sometimes develop unpleasant or unusual odors.

In other instances, closets may be come dank, pantries may become infested with insects, and dirty clothes hampers almost always have a mildewed, malodorous smell associated with them. Further yet, shoe storage areas, such as a shoe drawer in an armoire, may suffer from foot odors.

In addition to the above problems, these appliances and other enclosed spaces are usually in need of illumination. Typically, in refrigerators, a separate light is provided that is energized when the door is opened. In dishwashers, pantries, closets and others of the aforementioned areas there is typically no illumination provided.

Further yet, it is known that at least certain pest insects, such as cockroaches, moths, gnats, fruit flies and other food-infesting insects are adverse to ozone. In these instances, pantries and other food-storage areas may be kept insect-free by providing ozone to these areas.

In accordance with the foregoing, various embodiments of systems for providing ozone to a variety of types of enclosed spaces is shown and described. In addition, the ozone generator is configured so as to provide illumination to the area to which ozone is provided.

BRIEF DESCRIPTION OF THE DRAWINGS

FIG. 1 is a diagrammatic view of a refrigerator incorporating an ozone generator of the instant invention.

FIG. 1a is a side diagrammatic view of a refrigerator incorporating one embodiment of an ozone generator of the instant invention.

FIG. 2 is a diagrammatic view of an embodiment of the instant invention fitted or constructed just above a vegetable crisper in a refrigerator.

FIG. 3 is a diagrammatic view from above a vegetable crisper incorporating Applicant's invention.

DETAILED DESCRIPTION OF THE DRAWINGS

Figure 4:
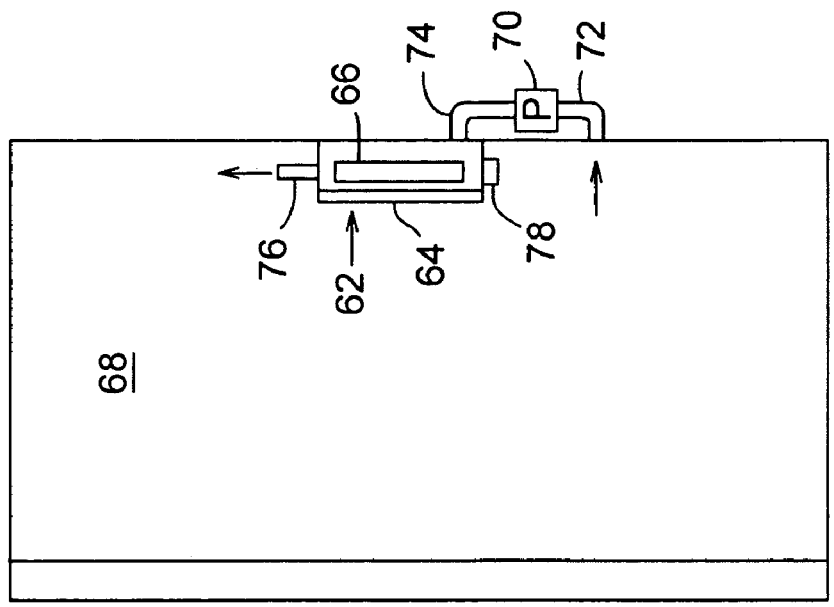
FIG. 4 is a side diagrammatic view of a refrigerator containing another embodiment of the instant invention.

In a simplest embodiment of the invention, and referring to FIG. 1, a refrigerator 10 is diagrammatically shown. Refrigerator 10 is provided with a vegetable crisper 12 within which vegetables and fruit are typically kept. In general, crisper 12 is configured as a drawer conventionally mounted in sliding relation within refrigerator 10. A tube 14 is mounted between a back side of crisper drawer 12 with an appropriate port so that when the crisper drawer is closed, an end of tube 14 communicates with an interior of crisper drawer 12. An opposite end of tube 14 communicates with an interior of an ozone generator 16, and an air pump 18 draws air from an interior of the refrigerator via an air line 20 and pumps the air through ozone generator 16 via an air line 21. Crisper 12 is provided with a plurality, or possibly only one, vent 22 to vent ozonated air to the interior of a main compartment of the refrigerator. Alternately, some or all of the ozonated air may be vented directly into refrigerator 10 via a line or opening 23 (dashed lines).

Ozone generator 16 may be constructed generally as shown in Applicant's patent application Ser. No. 09/717,903 now U.S. Pat. No. 6,428,756, which is incorporated in its entirety herein by reference. In addition, an ozone generator may be constructed as shown in Applicant's patent application Ser. No. 09/794,601 now abandoned, which is incorporated herein in its entirety by reference, and Applicant's patent application Ser. No. 10/061,752 now U.S. Pat. No. 6,723,233, which is also incorporated herein in its entirety by reference.

Particularly, ozone generator 16 may be configured as shown in FIG. 2 or 4 of the incorporated reference, or as shown in the other incorporated references, or it may be simply be configured as a square or rectangular enclosure. Where the ozone generator is square or rectangular, sides of the ozone generator would be either of visible light-emitting character or opaque, with a light-emitting panel 17 forming a front of the ozone generator. In other embodiments, the light-emitting side 17 of the ozone generator may be constructed flush with an interior wall of the refrigerator, or if as shown in FIG. 4 of the incorporated reference, the long sides of the ozone generator may be constructed flush with an interior side of the refrigerator, with ends being either opaque or visible light-emitting.

Referring to FIG. 1a, in order to prevent the phosphor coating from eroding and possibly contaminating the refrigerator, and for protecting the phosphor, the phosphor may be sandwiched between two sheets of transparent material. Next to ozone-producing mercury plasma tube 24, the sheet material 26 may be fluorinated ethylene propylene, a material that does not discolor after long exposure to ultraviolet radiation, or other material that does not become opaque or translucent in the presence of ultraviolet light, and sheet 28 may be glass, quartz, transparent plastic or other transparent material. As in the instance of a fluorescent tube, the phosphor is sufficiently thick so as to block ultraviolet light from escaping the ozone generator.

Referring to FIG. 2, an ozone generator 32 is shown mounted just above a vegetable crisper compartment 34. In this embodiment, an ultraviolet lamp 36 may be vertically mounted in a housing 38 having a front panel 40 configured to emit visible light when exposed to the ultraviolet radiation used to generate ozone. A ballast 42 for the plasma lamp may be mounted adjacent plasma tube 36 near opening 43 so that air heated by the plasma tube and ballast rises through opening 43 by convection, as shown by arrow 44, around the tube and ballast. The air, which being in a refrigerator, cools after it passes ballast 42 and tube 36 and spills over a top 46 of a compartment or tube that communicates with crisper compartment 34, as shown by arrow 48. The ozonated air then flows into the crisper 34, and from there may be vented by vents or openings 50 into the refrigerator. In this embodiment, at least some of the ozonated air is recycled back into the ozone generator. Alternately, opening 43 may communicate with the crisper so as to form a closed loop system between the ozone generator and crisper. As described in the foregoing, front panel 40 provides visible light to the interior of the refrigerator. In yet another alternate embodiment, a small fan may be located at opening 43 so as to actively drive air through the ozone generator and crisper.

In the embodiment of FIG. 3, an ultraviolet plasma lamp 52 is mounted, typically horizontally, behind crisper compartment 54, with a visible light-emitting plate 56 mounted between lamp 52 and a rearward end of crisper 54. In this embodiment, the crisper compartment would be constructed of transparent or translucent material, so that the walls and drawer of the crisper compartment would glow. Here, ozone may be circulated through compartment 54 by openings 58 and 60, either by a fan located at one of the openings, or by convection by positioning one of the openings at a lower location at the rear of the compartment and the other opening at an upper location at the rear of the compartment. Openings or spaces are provided around the plasma tube to allow free circulation of air between the plasma tube and crisper compartment. Where the crisper compartment is a drawer, communicating openings would be provided between the ozone generator portion and a rear of the drawer.

In another simple embodiment, as shown in FIG. 4, an ozone generator 62 configured as described with a visible light-emitting panel 64 covering a plasma tube 66 is located in a back of a refrigerator 68. An air pump 70 may be provided to pump air from refrigerator 68 via air lines 72 and 74 to the ozone generator 62, with the ozonated air simply being vented by an opening or tube 76 into the refrigerator. As described, an opening 78 may be provided at a bottom of ozone generator 62 so that air may circulate through the ozone generator by convection, or a small fan (not shown) may be provided to circulate air upward through the ozone generator.

In the above embodiments, the ozone generator may be left "ON" continuously. Thus, ozone and visible light is continually being generated. Of course, airflow through these ozone generators is regulated or may be regulated so that ozone levels are maintained at a relatively low, non-irritating level.

Figure 5A:
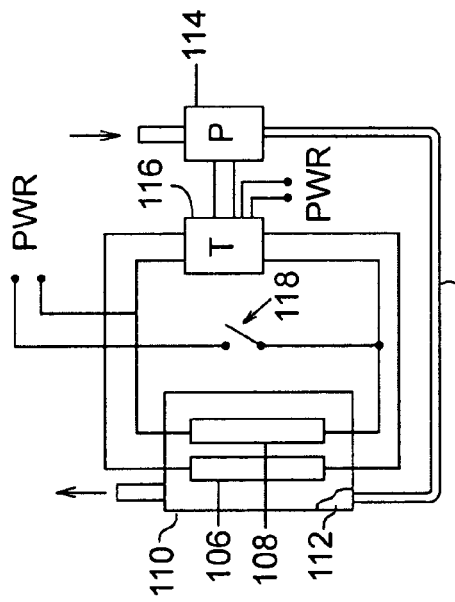
FIG. 5a is a diagrammatic view of details of construction of the embodiment shown in FIG. 5.
Figure 5:
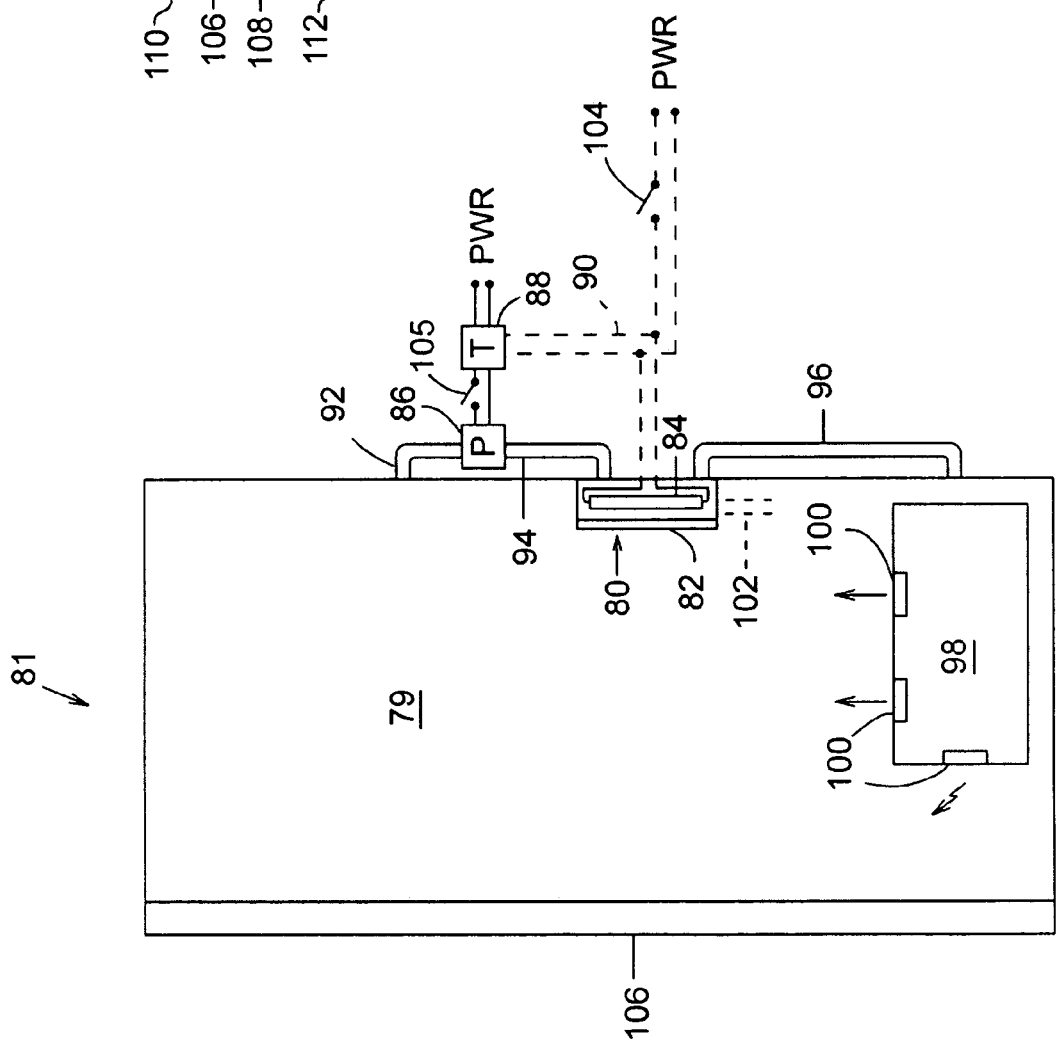
FIG. 5 is a side diagrammatic view of another embodiment of the instant invention.

As shown in FIG. 5, an embodiment is disclosed wherein ozone in an interior 79 of refrigerator 81 is cycled alternately to high and low levels. Here, an ozone generator 80 is constructed having a front, visible light-emitting panel 82 mounted in front of an ultraviolet plasma tube 84. An air pump 86 is electrically coupled to a timer circuit 88 that controls operation of pump 86, and possibly plasma tube 84, as shown by dashed lines 90 which are illustrative of electrical connections between timer circuit 88 and a ballast of tube 84. Air lines 92, 94 and 96 provide an air flow path between an interior 79 of the refrigerator, through pump 86, through ozone generator 80 and into a crisper compartment 98, respectively. From crisper compartment 98 ozonated air may be vented into the main compartment or interior 79 of the refrigerator through vents 100. As stated above, some or all of the ozone may be provided to interior 79 of the refrigerator by a tube or opening 102 (dashed lines) directly from ozone generator 80.

In this embodiment, timer 88 controls operation of the ozone generator so as to cycle operation thereof to periodically bring ozone levels in the refrigerator up to a relatively high, sanitizing or deodorizing level, and then allow ozone levels in the refrigerator to fall. Such cycling may be on the order of energizing the ozone generator for a relatively short period of time, such as, but not limited to, 10–30 minutes or so. The ozone generator is then switched "off" for a period of time, such as, but not limited to, 2–6 hours or so in order to allow ozone levels in the refrigerator to fall. In this embodiment, power to the plasma tube 84, or the ozone generator itself, may be controlled by a door switch 104 coupled to energize tube 84 when a door 106 of the refrigerator is opened, as should be apparent to one skilled in the art. This energizes lamp 84 and pump 86 while door 106 is opened, providing light to the interior of the refrigerator. In the instance where the pump operates concurrently with the plasma tube 84, an amount of ozone produced by the ozone generator is small during the few seconds the refrigerator is opened, but would probably serve to periodically deodorize an interior of the refrigerator. When the door 106 is opened for longer periods of time, such as for cleaning or servicing of the refrigerator, another switch 105 may be provided to switch air pump 86 "OFF" while the plasma tube is "ON" responsive to the door switch in order to minimize the ozone levels produced by the ozone generator.

Referring to FIG. 5a, another embodiment of an ozone generator of the present invention is shown. Here, a pair of plasma tubes 106, 108 are provided within an enclosure 110 of the ozone generator. A front cover 112, shown broken away, is configured as described to emit visible light when exposed to ultraviolet radiation. A pump 114 is coupled to electrical power via a timer 116, which may be configured to energize plasma tubes 106, 108 independently. Pump 114 is coupled to provide ozone to the crisper compartment, main portion 79 of the refrigerator, or both, by an air line 115. In addition, plasma tube 108 may be separately coupled to electrical power via a door switch 118 so as to energize lamp 108 when the refrigerator door is opened.

Lamp 106 is of a type that provides ultraviolet light that includes a wavelength of 185 nanometers, this wavelength producing ozone as air is pumped through the ozone generator. Plasma tube 108 is of a type that includes radiation at 254 nanometers, which destroys ozone and which also causes ozone to react in a process known as advanced oxidation. In this process, lamp 106 is operated for a relatively long period of time, such as 1–4 hours or so, to produce a relatively high concentration of ozone in the enclosed area. After these relatively high levels are attained, lamp 108 is energized, which breaks down the ozone into a molecule of diatomic oxygen and a free ozone atom, which is highly reactive. In addition, the free oxygen atom is very energetic due to being struck by a photon of a wavelength of 185 nm to create the ozone molecule and a photon of a wavelength of 255 nm to break apart the ozone molecule. This energetic free oxygen atom will react with hydrogen peroxide, which is present in atmospheric moisture that has been exposed to ozone or in water exposed to ozone, to form hydroxyl radicals. These hydroxyl radicals will then break down many compounds, such as cyanides, trivalent chromium, and many difficult-to-destroy humid organic materials that tend to produce odors.

With the above-described construction, and as stated, the lamp 106 may be operated for several hours to produce the high level of ozone, after which lamp 108 is also energized for a short period, such as 30 minutes or so. This breaks the existing ozone apart, producing free oxygen atoms that react with any hydrogen peroxide present to produce hydroxyl radicals. These hydroxyl radicals then react as described to break down sources of methane and other odors. In addition, operating both lamps 106 and 108 as described has the effect of forming ozone and immediately breaking it down to form energetic free oxygen molecules. After operating both lamps for a shorter period of time as described, lamp 108 is operated for a longer period of time, such as 1–2 hours or so, which lowers ozone levels and provides germicidal ultraviolet radiation. This cycle may be repeated indefinitely, or at periodic intervals, such as once a day, 2–3 times a week, etc.

Figure 6A:
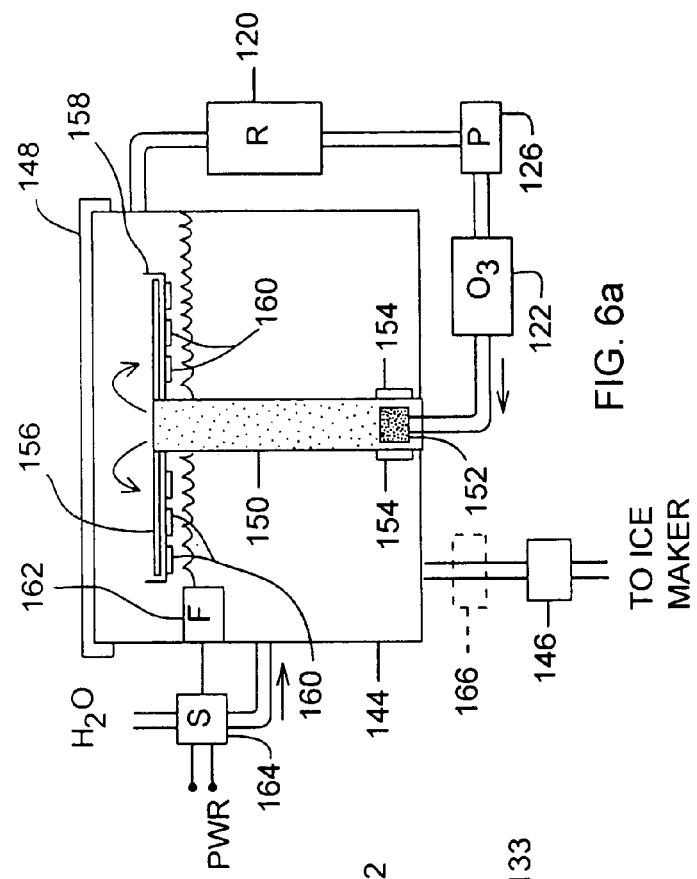
FIG. 6a is a view illustrating details of construction of the embodiment shown in FIG. 6.
Figure 6:
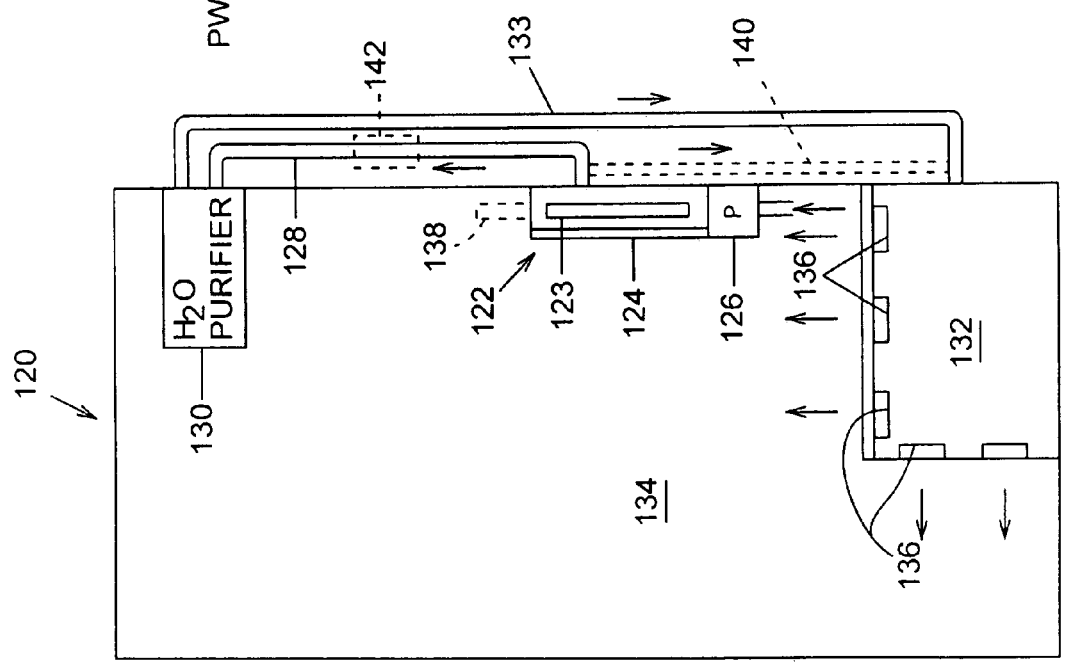
FIG. 6 is a side diagrammatic view of a refrigerator incorporating an embodiment of the instant invention directed toward an icemaker.

Referring to FIG. 6, a refrigerator 120 is shown wherein an ozone generator 122 having a front, visible light-emitting panel 124 is provided, with a pump 126 being incorporated into the ozone generator so as to pump air therethrough, or the air pump may be separate from the ozone generator. In addition, the ozone generator 122 may contain a single plasma tube 123 for generating ozone, or it may contain a second plasma tube as described for FIG. 5a to incur the advantages of the advanced oxidation processes. In this embodiment, ozonated air is pumped through an air line 128 to an automated icemaker 130 in order to purify and deodorize water used for making ice. Outgassing from the water purification process, which still contains ozone, may be circulated back to a crisper portion 132 of the refrigerator via an air line 133 and then into the main portion 134 of the refrigerator via vents 136 as described in the foregoing. In another embodiment, a portion of the ozone may be directed into the refrigerator by a tube or opening 138 (dashed lines) or a portion of the ozone may be directed to the crisper via air line 140 (dashed lines). In another version of this embodiment, the ozone may primarily be directed to the refrigerator, crisper or both, and switched to the icemaker for a selected period of time, such as 30 minutes or so, by an air valve 142 (dashed lines) responsive to a signal that activates filling of the icemaker water reservoir wherein ice forms in order to purify the water used to fill the icemaker.

Referring to FIG. 6a, one embodiment of a water purification system for an icemaker is shown. Here, a water reservoir 144 holds purified water to be used in the icemaking process, with a water valve and solenoid 146 in the refrigerator regulating flow of water to an icemaking receptacle. In order to prevent water in reservoir 144 from freezing, reservoir 144 is located outside the freezer portion of the refrigerator, such as in a main portion 134 of the refrigerator or within the cabinet of the refrigerator but outside the freezer portion, with a door or panel on an outside of the refrigerator providing access to reservoir 144. The reservoir 144 is enclosed by a removable top or cover 148, with a tubular column 150 located within the reservoir 144. A diffuser 152 is located at a bottom of column 150, with a top of column 150 being open and at least one opening 154 at a bottom of column 150 communicating with reservoir 144. As described for FIG. 6, air is pumped by pump 126 from refrigerator 120 through ozone generator 122 and into diffuser 152, which breaks the flow of ozone into small bubbles that rise upward through column 150. Here, column 150 also serves as a contact region wherein the water is exposed to ozone gas, sanitizing the water and causing many organic and inorganic materials therein to precipitate. At the top of column 150, the water, pumped by the rising bubbles, pours over the top of the column and onto a filter, which may be a paper filter 156 supported by a tray 158. Water then is filtered as it passes through filter 156, after which it drips or flows back into reservoir 144 via openings 160 in tray 158. A float or other water level switch 162 is coupled to a water valve 164, and is used to regulate a water level in reservoir 144 so that the water level is maintained close to a bottom of tray 158 in order to allow water pumped by rising bubbles to flow over a top of column 150. In an alternate configuration, the try 158 and filter 156 may be eliminated, and the reservoir made just sufficiently large so as to contain water for approximately one or two fillings of the ice maker. In this instance, an easily replaceable cartridge filter 166 (dashed lines) may be located just prior to water valve 146. The water column 150 and diffuser 152 would generally remain the same.

Figure 6B:
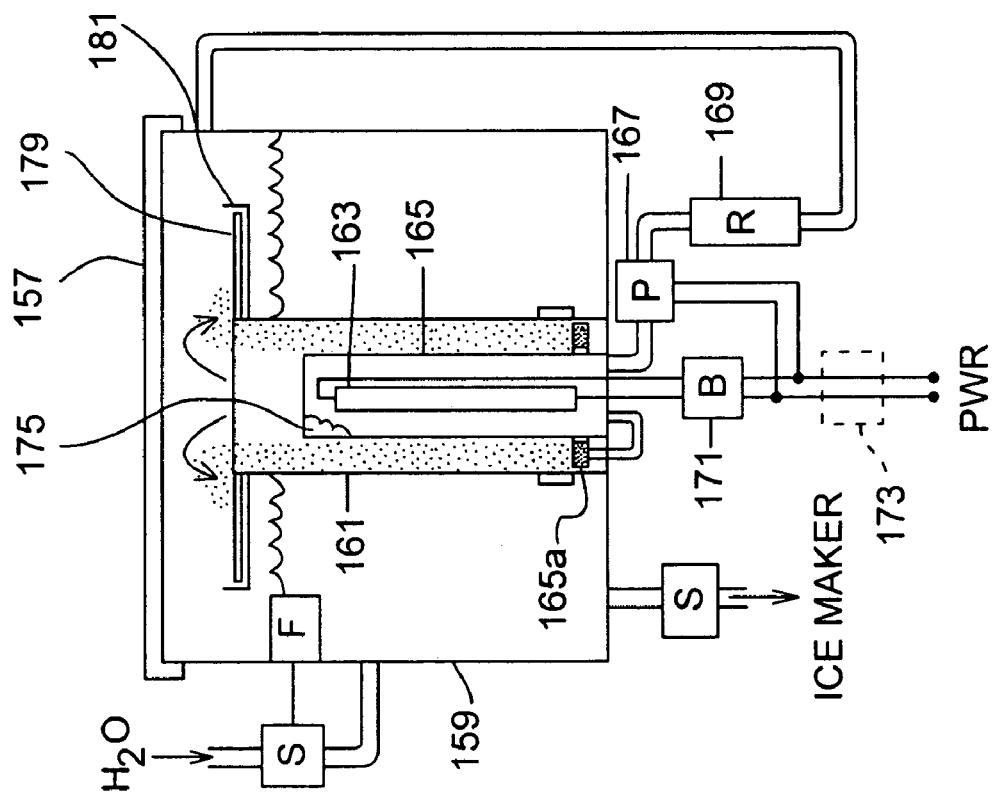
FIG. 6b is a diagrammatic view of details of construction of another embodiment of the invention shown in FIGS. 5 and 6.

In another embodiment of an advanced oxidation system, and referring to FIG. 6b, a water reservoir 159 contains a water column 161 having at least one opening in a lower end as described for FIG. 6a, except the ultraviolet lamp 163 is mounted inside a generally watertight, transparent housing 165 within the water column 161. A diffuser 165a, which may be tubular or of other configuration is positioned at a bottom of an inside of water column 161, and receives ozonated air from an interior of housing 165. An air pump 167 is coupled to pump air from refrigerator 169 into housing 165 where ozone is generated. Pump 167 and lamp ballast 171 may be coupled so as to be energized by any of the methods described above, such as by a door switch, or by a timer 173 (dashed lines) operable to cycle ozone levels high and low, operate at regular intervals, operate only during a period of non-use, such as at night, or operate partially or only responsive to an icemaker in the refrigerator being refilled with ice. In addition, the water reservoir 159 and removable top 157 may be constructed in a rectangular configuration so as to provide a front panel 175 (shown partially broken away) adjacent plasma tube 163, the front panel emitting visible light when tube 163 is energized. The reservoir 159 may then be mounted in a location, such as in a rearward wall, so that front panel 175 is generally flush with an interior wall of the refrigerator so as to provide illumination to an interior thereof. In this instance, a small water pump (not shown) may be needed to pump the water against gravity to the icemaker. Alternately, the reservoir 159 may be mounted in a wall adjacent to the icemaker to provide illumination to the freezer portion of the refrigerator. Where the visible light-emitting panel provides light to an interior of a refrigerator, housing 165 may be configured so as to extend the panel 175 away from reservoir 159 in order to provide clearances to mount panel 175 generally flush with an interior of a refrigerator or freezer. In the instance where Applicant's ozone generator is installed in commercial icemakers, such as found in motels, hotels restaurants or the like, the visible light may be used to illuminate an interior of the icemaker, or used to illuminate from behind an exterior sign for advertising or other purposes. Otherwise, the ozone generator may be remotely located from the reservoir as shown in FIG. 6a, with the water reservoir being generally round when viewed from above. As described for FIG. 6a, a water valve controlled by a float switch may be used to regulate a water level in the reservoir, and a solenoid controlled valve in the refrigerator controls refilling of an ice receptacle wherein water freezes. In this embodiment, at least some of the walls of housing 165 not used to generate visible light may be constructed of a material that passes ultraviolet light of a wavelength of 254 nm but blocks light of a wavelenth of 185 nm. This promotes the advanced oxidation process as described for FIG. 6a by breaking down ozone in the water to free a highly reactive oxygen molecule next to the water column, which then reacts almost instantly with any impurities in the water. As described above, the water in the water column bubbles over a top thereof and is filtered by a filter 179 in a tray 181 or the like, with the filtered water being recycled through and past the water column for a selected period of time to allow the quantity of water in the reservoir to be purified prior to being applied to the icemaker. Also, instead of a paper filter, a cartridge filter may be employed between the reservoir and ice maker, as described for filter 166 of FIG. 6a.

Figure 7:
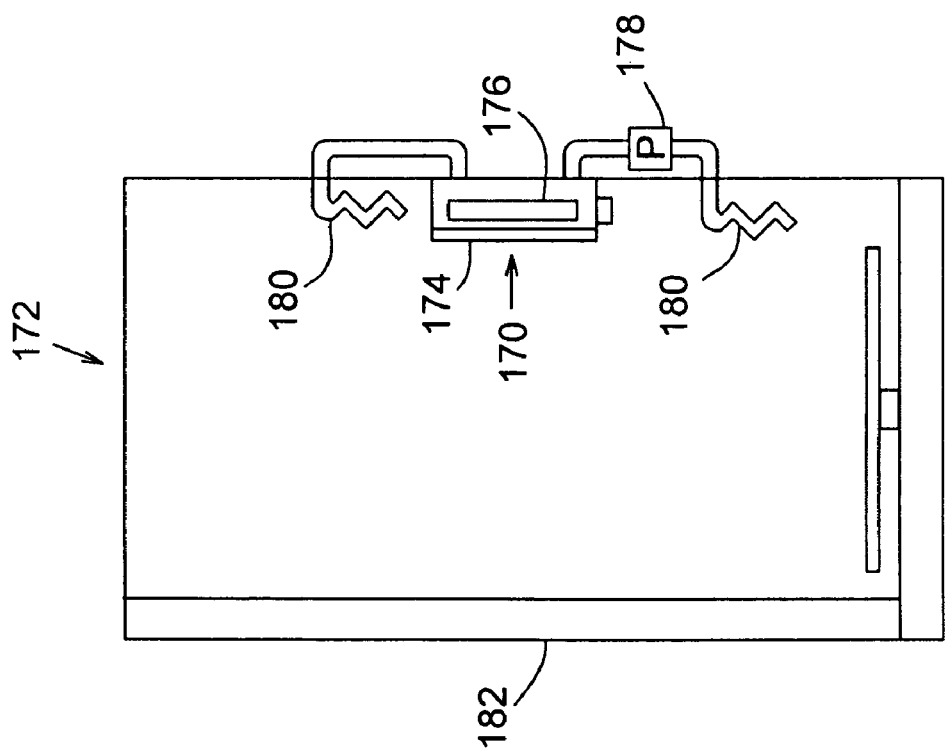
FIG. 7 is a side diagrammatic view of an embodiment of the instant invention incorporated in a dishwasher.

Referring to FIG. 7, a combined ozone generator and light source 170 is shown incorporated into a dishwasher 172. As described above, a front panel 174 is configured to provide visible light when exposed to ultraviolet light, with a plasma tube 176 providing the ultraviolet light. An air pump 178 pumps air through the ozone generator, with devices such as serpentine tubes or check valves preventing water and chemicals from the dishwasher from entering the ozone generator. In operation, this embodiment may operate in cycles in conjunction with a timer as described above, or operate continuously while a door 182 of the dishwasher is closed. Also as described, the ozone generator 170, or at least the plasma tube 176, may be energized momentarily responsive to a door switch so that the interior of the dishwasher is illuminated when door 182 is opened. During operation of the dishwasher, the ozone generator and air pump are preferably switched to an "OFF" state, although it may be discovered that ozone may assist dishwashing chemicals to clean and sanitize articles washed in a dishwasher. In this instance, the ozone generator would be left "ON" during at least some cleaning and rinsing cycles.

Figure 8:
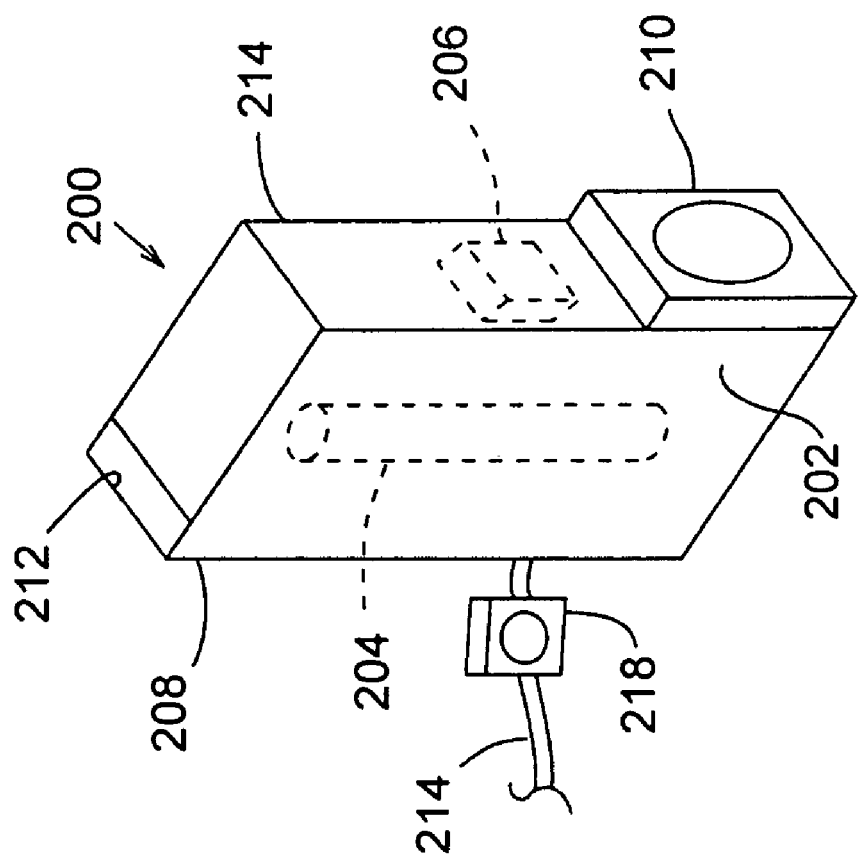
FIG. 8 is a diagrammatic view of an ozone generator of the instant invention adapted to be placed in an enclosed space.

Referring to FIG. 8, a self-contained retrofit ozone generator and light source 200 is shown. A front panel 202 is constructed as described incorporating a visible light-emitting phosphor compound, and a plasma tube 204 (dashed lines) and associated ballast 206 (dashed lines) mounted inside an enclosure 208 of the ozone generator. A fan or pump 210 pumps air through the ozone generator, with ozonated air exiting the ozone generator from a slot 212. On a rear side 214 of the ozone generator, hooks or slots may be provided in order to hang the ozone generator on a wall of a cabinet, pantry or closet, or the ozone generator may simply be placed on a shelf of a cabinet, pantry or closet. Additionally, such an ozone generator may be mounted in a laundry hamper, as by a wire hook attached to the ozone generator and looping over an upper edge of the hamper between a lid and body of the hamper. A power cord 214 may be conveniently routed to a power source, and a timer 218 may be used to selectively operate the ozone generator for selected periods of time at selected times of the day. With this configuration, ozone generator 200 may be placed in any confined space needing deodorizing and sanitizing as well as illumination.

Figure 9:
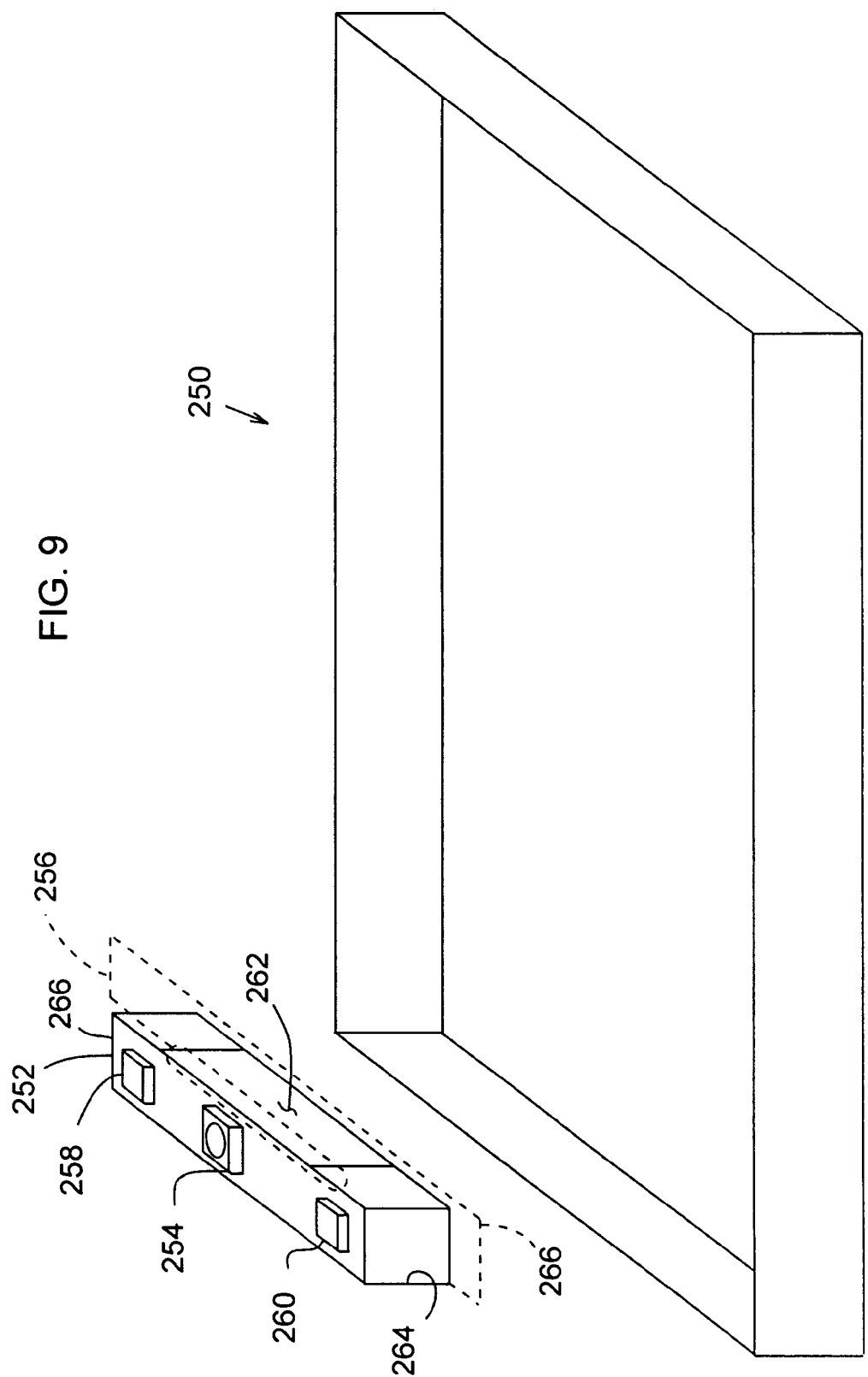
FIG. 9 is an embodiment of Applicant's invention for use over a cat litter box.

FIG. 9 illustrates another embodiment of the invention for use in conjunction with a cat litter box 250. Here, a hollow, rectangular housing 252 open at both ends is constructed on the order of from about 1–2 feet or so, with a small fan 254, such as an 80 mm fan used to cool personal computers, generally centrally mounted to an exterior of housing 252 and over an opening therein so as to circulate outside air through an interior of housing 252. An ultraviolet plasma tube 256 (dashed lines) is mounted in housing 252, with a ballast 258 mounted wherever convenient, such as on an outside of housing 252. A timer 260 may be used to operate the plasma lamp 256 and fan 254 for selected periods of time or for selected cycles of time, and may further incorporate a motion detector for sensing presence of a cat in the cat box. In this instance, the motion detector may be used to interrupt operation of the ozone generator, as such operation may discourage a cat from using the cat box. Here, a delay circuit may also be incorporated in circuit with the motion detector in order to energize the ozone generator, or resume its operation, after a cat has left the box. This delay may be on the order of 2–5 minutes or so. In other modes of operation, the timer and delay circuit may be energized for a selected period of time, such as 30 minutes or so, only after a cat has used the box. If desired, a front panel 262 may be provided that emits visible light in the presence of ultraviolet light, and a manual switch may be provided to allow an owner of the cat box to switch "ON" the ozone generator to produce visible light when scooping litter from the box or for simply operating the ozone generator continuously. In this embodiment, malodorous air from the cat box is drawn into each of ends 264 and 266, and is passed over ultraviolet tube 256, where ozone created by the tube destroys the odors. The air is then blown upward by the fan. Alternately, a fan would be located on a bottom side of housing 252, and draw the malodorous air into the housing and blow the deodorized air out ends of the housing. In any instance, it is desirable to mount the ozone generator in a location over the cat box, such as on a shelf 266 (dashed lines) along an end or one side of the cat box. Alternately, a removable triangular structure may be incorporated into the cat box or ozone generator so that two opposed sides of the cat box are enclosed, with the ozone generator centered above the cat box with ends 264 and 266 adjacent open sides thereof. Still further, other structures to cover the cat box on three sides are possible, with the ozone generator drawing air from an interior thereof in order to deodorize the air.

In most embodiments of the invention wherein the ozone generator is operated continuously, such operation may be at night or other times when the appliance is not being used, or in the case of a refrigerator, the door is not being frequently opened. Where the embodiment of FIG. 8 is used in a confined space, such as pantries, closets and the like, continuous operation would typically occur during periods when doors of such areas are closed, such as at night.

It should be apparent to those skilled in the art that minor details such as wiring a ballast of an appropriate electrical capacity is necessary to the plasma tubes of the present invention. Additionally, the wiring of timers as described to various embodiments of the instant invention should be well within the domain of one skilled in the art, as is selection of the type of fittings and fasteners required to assemble any of the disclosed embodiments. Further, housing that are integral to the instant invention may be molded integrally with various parts of a refrigerator or other appliance, or may be separate components added to parts of a refrigerator or other appliance.

Having thus described my invention and the manner of its use, it should be apparent to one skilled in the art that incidental changes may be made thereto that fairly fall within the scope of the following appended claims, wherein I claim:

1. A combined ozone generator and refrigerator comprising:
   a housing mounted in said refrigerator and having an air inlet and an air outlet for allowing an airflow through said housing, said air outlet coupled to provide said airflow to an interior of said refrigerator,
   an ultraviolet light source in said housing for generating ozone in said airflow and,
   at least a portion of said housing being constructed from a material configured to emit visible light to provide illumination to said interior of said refrigerator when exposed to said ultraviolet light source, said portion of said housing being in light-transmissive relation with an interior of said refrigerator.

2. A combined ozone generator and refrigerator as set forth in claim 1 wherein said air outlet of said ozone generator is coupled to a vegetable crisper in said refrigerator.

3. A combined ozone generator and refrigerator as set forth in claim 2 further comprising airflow outlet vents in said vegetable crisper to provide ozone generally from an interior of said vegetable crisper to said interior of said refrigerator.

4. A combined ozone generator and refrigerator as set forth in claim 3 wherein said ozone generator is constructed just over a rear portion of said vegetable crisper.

5. A combined ozone generator and refrigerator as set forth in claim 4 wherein said airflow from said ozone generator is provided through openings in a rear of said vegetable crisper.

6. A combined ozone generator and refrigerator as set forth in claim 4 wherein said ultraviolet light source is a plasma discharge tube mounted vertically in said housing, with said air inlet at a lower end of said housing and a ballast for said plasma discharge tube mounted near said air inlet, and said air outlet being at a top of said housing whereby air is warmed by said ballast and flows upward by convection, is cooled and falls through said air outlet into said vegetable crisper.

7. A combined ozone generator and refrigerator as set forth in claim 2 wherein said airflow through said housing is developed by a fan.

8. A combined ozone generator and refrigerator as set forth in claim 1 wherein said material configured for emitting visible light is a phosphor material, said phosphor material disposed between two protective layers of a sheet material.

9. A combined ozone generator and refrigerator as set forth in claim 1 wherein said refrigerator further comprises an automatic icemaker, with at least a portion of said airflow containing ozone provided to water purification apparatus comprising:
   a water reservoir with a removable top,
   a hollow tubular member in said reservoir, said hollow tubular member having openings at a lower end thereof in communicating relation with water in said water reservoir,
   a water level controller for maintaining a water level in said reservoir to just below a top of said hollow tubular member,
   a pump configured to pump ozone under pressure from said ozone generator,
   a gas diffuser positioned in said lower end of said hollow tubular member, said gas diffuser coupled to receive ozone from said pump,
   a particulate filter for filtering said water after exposure to said ozone,
   whereby ozone is bubbled up through said water in said hollow tubular member where said water is spilled over said top of said hollow tubular member and returned to said water reservoir.

10. A combined ozone generator and refrigerator as set forth in claim 9 wherein said ultraviolet light source is incorporated in said water reservoir by a housing having at least an ultraviolet light-transparent portion so as to expose said water through which said portion of airflow containing ozone is bubbled to said ultraviolet light, and wherein said visible light is provided to a freezer portion of said refrigerator.

11. A combined ozone generator and refrigerator as set forth in claim 9 further comprising a timer coupled to operate said ozone generator and said pump for selected periods of time.

12. A combined ozone generator and refrigerator as set forth in claim 11 wherein offgassing containing ozone from said water is returned to said interior of said refrigerator.

13. A combined ozone generator and refrigerator as set forth in claim 9 wherein said particulate filter further comprises a porous filter medium support tray mounted just above said water level, and replaceable filter medium resting on said tray whereby said water spilling over a top of said hollow tubular member is spilled onto said replaceable filter medium and returned to said reservoir as particulate-filtered water.

14. A combined ozone generator and refrigerator as set forth in claim 9 wherein said particulate filter is a cartridge filter coupled to filter water from said reservoir.

15. A combined ozone generator and refrigerator as set forth in claim 1 wherein said ultraviolet light source further comprises:
   a first ultraviolet light source that emits ultraviolet radiation predominately at about 185 nanometers for generating ozone,
   a second ultraviolet light source that emits ultraviolet radiation predominately at a wavelength of about 254 nanometers for destroying ozone.

16. A combined ozone generator and refrigerator as set forth in claim 15 further comprising a timer for operating said first ultraviolet light source for a selected period of time to create said ozone, and then operating said second ultraviolet light source for a selected period of time to destroy said ozone.

17. A combined ozone generator and refrigerator as set forth in claim 1 wherein said housing is mounted within a wall of said refrigerator.

18. A combined ozone generator and refrigerator as set forth in claim 1 further comprising an electrical door switch coupled to energize said ozone generator to provide illumination to an interior of said refrigerator when a door to said refrigerator is opened, and also deodorizing an interior of said refrigerator responsive to opening said door.

19. A combined ozone generator and refrigerator as set forth in claim 1 further comprising a timer coupled to said ozone generator and configured to operate said ozone generator for selected periods of time.

20. An icemaker for a refrigerated area comprising:
   an ozone generator comprising:
      a housing mounted in said ice maker and having an air inlet and an air outlet for allowing an airflow through said housing, said air outlet coupled to provide said airflow to an interior of said icemaker,
      an ultraviolet light source in said housing for generating ozone in said airflow, and
      at least a portion of said housing being constructed from a material configured to emit visible light to provide illumination to said interior of said icemaker when exposed to said ultraviolet light source, said portion of said housing being in light-transmissive relation with an interior of said icemaker,
   an air pump coupled to drive air through said housing and,
   water purification apparatus further comprising:
      a water reservoir,
      a hollow tubular member in said water reservoir and having at least one opening at a lower in thereof in communicating relation with water in said water reservoir,
      a diffuser in said lower end of said hollow tubular member,
      a water level controller disposed for controlling a level of said water to just below a top of said hollow tubular member and,
      a particulate filter for removing particulates in said water provided to said icemaker.

21. An icemaker for a refrigerated area as set forth in claim 20 wherein said particulate filter further comprises a removable filter medium tray mounted to a top of said hollow tubular member, with removable filter medium on said filter medium tray so that water flowing over said top of said hollow tubular member falls on said removable filter medium and passes through said filter medium tray to said reservoir.

22. An icemaker for a refrigerated area as set forth in claim 20 wherein said particulate filter further comprises a filter cartridge coupled to filter water flowing from said reservoir.

* * * * *